United States Patent [19]
Zettler et al.

[11] Patent Number: 6,051,253
[45] Date of Patent: *Apr. 18, 2000

[54] PRODUCTION OF SOLID DRUG FORMS

[75] Inventors: Hans Dieter Zettler, Grünstadt; Michael Schiessl, Hassloch; Jörg Breitenbach, Mannheim; Joerg Rosenberg, Ellerstadt, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/886,286

[22] Filed: Jul. 1, 1997

[30]  Foreign Application Priority Data

Jul. 23, 1996 [DE] Germany ............... 196 29 753

[51] Int. Cl.[7] ..................................... A61K 9/20

[52] U.S. Cl. ........................ 424/465; 424/464; 424/467

[58] Field of Search ................... 424/464, 465, 424/467

[56]  References Cited

U.S. PATENT DOCUMENTS

| | | | |
|---|---|---|---|
| 1,419,147 | 6/1922 | Kloepping | 424/464 |
| 4,059,382 | 11/1977 | Kobayashi et al. | 425/446 |
| 4,801,460 | 1/1989 | Goertz et al. | 424/465 |
| 4,880,585 | 11/1989 | Klimesch et al. | 264/141 |
| 4,957,681 | 9/1990 | Klimesch et al. | 264/211 |
| 5,073,379 | 12/1991 | Klimesch et al. | 424/467 |

FOREIGN PATENT DOCUMENTS

| | | |
|---|---|---|
| 957875 | 2/1957 | Germany . |
| 19539361 | 10/1995 | Germany . |
| 2192128 | 1/1988 | United Kingdom . |

*Primary Examiner*—James M. Spear
*Attorney, Agent, or Firm*—Keil & Weinkauf

[57] ABSTRACT

Solid drug forms are produced by mixing and melting at least one pharmacologically acceptable polymeric binder and at least one pharmaceutical active ingredient, with or without conventional pharmaceutical additives, in the absence of a solvent to give a plastic mixture and shaping the mixture to the required drug form by extrusion, where the shaping takes place in two steps, with the extrudate being broken into shaped articles in a first step, and these shaped articles being rounded off in a second step in the plastic state.

6 Claims, 3 Drawing Sheets

PRODUCTION OF SOLID DRUG FORMS

The present invention relates to a process for producing solid drug forms by mixing and melting at least one pharmacologically acceptable polymeric binder and at least one pharmaceutical active ingredient, with or without conventional pharmaceutical additives, in the absence of a solvent to give a plastic mixture and shaping the mixture to the required drug form.

Classical processes for producing solid drug forms, in particular tablets, are carried out batchwise and comprise a plurality of stages. Pharmaceutical granules represent an important intermediate therein. Thus, for example, the book "Pharmazeutische Technologie", edited by Professors Bauer, Frömmig and Führer, Thieme Verlag, pages 292 et seq. discloses that drug forms can be obtained from the melt by dry granulation. It is described how melt solidification granules can be produced either by melting and shock solidifying, by casting and comminuting or by spray solidifying in spray towers. One problem with this process is the accurate shaping which is necessary to produce drug products. Irregular particles or fragments are frequently produced so that the resulting shape by no means corresponds to conventional drug forms, and granules therefore have but little importance as a drug form on their own. The production of the required solid drug forms requires the use of further process steps such as compression in tableting machines. This is time- and cost-intensive.

A considerably simpler continuous process for producing solid drug forms has been known for some time and entails a solvent-free melt of a polymeric binder containing active ingredient being extruded, and the extrudate being shaped to the required drug form, for example in a calender with molding rolls, see EP-A-240 904, EP-A-240 906 and EP-A-337 256 and EP 358105. Although specific shaping can be achieved in this way, this process has the considerable disadvantage that there are flashes between the tablets or on the tablets, and these must be removed in subsequent process steps. Processes of this type are elaborate and, in many cases, involve product losses in the form of damaged tablets which cannot always be recycled to the process for various reasons.

It is an object of the present invention to provide a simple and cost-effective process for producing solid drug forms, in particular tablets of defined shape.

We have found that this object is achieved by shaping the extruded plastic mixture in two separate steps, namely cutting the extrudate and rounding off the resulting pieces in the plastic state.

The present invention therefore relates to a process for producing solid drug forms by mixing and melting at least one pharmacologically acceptable polymeric binder and at least one pharmaceutical active ingredient, with or without conventional pharmaceutical additives, in the absence of a solvent to give a plastic mixture and shaping the mixture to the required drug form by extrusion, wherein the shaping takes place in two steps, with the extrudate being broken into shaped articles in a first step, and these shaped articles being rounded off in a second step in the plastic state.

According to the invention, the plastic mixture is first extruded to a continuous extrudate using a suitable die. The shape of the die depends on the required drug form. Suitable examples are round-section dies or coextrusion dies such as ring-shaped dies. Coextrusion dies are used to produce open or closed drug forms which have at least two layers. One of these layers comprises an active ingredient, and the other layer can be free of active ingredient or comprise another active ingredient. Further details are to be found in DE 195 39 361.9.

However, round-section dies are preferably used, in which case the plastic mixture is converted into an extrudate with a circular cross-section.

The die design depends on the polymeric binder used and the required drug form. The dies are preferably arranged on a horizontal line, with the distances between the holes generally being a multiple of their diameter. After emerging from the die, the extrudate is split up or broken down, preferably by cutting or chopping. The timing of the breaking down depends on the extrusion rate and the required drug form. It is advantageous in this connection to support the extrudates mechanically after emergence from the die, eg. by a horizontal plate or a circulating belt. This results, for example, in cylinders with a defined length L and a defined diameter D. The L/D ratio may vary depending on the required drug form. If the ratio is >1 (eg. $\geq 2$), oblong tablets are obtained, and when it is $\leq 1$, or discoidal tablets can be obtained.

The splitting-up device is preferably controlled separately for each extrudate. The required length of the shaped article can be measured, for example, by an optical system. When the required length is reached (distance from the breaker plate), this optical system gives a signal to a cutting device which, independently of the other cutting devices is assigned to one hole in each case, cuts off the extrudate and swings back into its initial position.

The resulting shaped articles are rounded off according to the invention in a second step. In this connection, rounding off means rounding the edges and corners of the shaped article with its weight being negligibly changed. The rounding off is effected by contacting the shaped article with one or more rounding-off tools. During this, either the shaped article or the rounding-off tool(s) executes a movement, while the other is at rest. It may also be advantageous in certain cases for both to move in order to achieve a particular shaping. The movement of the shaped article, eg. rolling, can be achieved, for example, by placing it between a stationary and a moving surface, preferably two plates or one plate and a moving belt. The movement of the rounding-off tool can be achieved in a conventional way.

The rounding-off tool preferably used is a curved, in particular semicircular, jaw which is, in particular, a metallic component which has an essentially concave shape on the side facing the cylindrical sections.

It is a precondition for the rounding-off step that the shaped article is in the plastic state. This can be achieved by, for example, delaying the cooling step for the shaped article and/or making the time between emergence of the extrudate from the die and the rounding off as short as possible. Another possibility is to control the temperature of the rounding-off tool, eg. by heating, so that when it makes contact with the shaped article the latter has suitable plasticity.

After the shaping step, the drug forms are allowed to cool and solidify, eg. on a cooling belt.

The present process for producing solid drug forms also comprises the mixing and melting of at least one pharmacologically acceptable polymeric binder and at least one pharmaceutically active ingredient, with or without conventional pharmaceutical additives, in the absence of a solvent to give a plastic mixture.

These process steps can be carried out in a conventional way, for example as described in EP-A-240 904, EP-A-337 256 and EP-A-358 105, the contents of which are incorporated herein by reference.

The components can be first mixed and then melted and homogenized. However, it has proven preferable, especially on use of sensitive active ingredients, first to melt and premix the polymeric binder, with or without conventional pharmaceutical additives, operating the stirred vessels, stirrers, solid mixers etc. alternately where appropriate, and then to mix in (homogenize) the sensitive active ingredient(s) in the plastic phase with very short residence time in intensive mixers. The active ingredient(s) can be employed in solid form or as solution or dispersion.

The melting and mixing take place in an apparatus customary for this purpose. Particularly suitable are extruders or heatable tanks with stirrer, eg. kneader (such as the type mentioned hereinafter).

It is also possible to use mixing apparatus of the types employed for mixing in plastics technology. Examples of suitable apparatus are described in "Mischen beim Herstellen und Verarbeiten von Kunststoffen", H. Pahl, VDI-Verlag, 1986. Particularly suitable for mixing are extruders and dynamic and static mixers, and stirred vessels, single-screw stirrers with stripper devices, in particular paste stirrers, multi-screw stirrers, in particular PDSM mixers, solids mixers, and, preferably, mixing/kneading reactors (eg. ORP, CRP, AP, DTB supplied by List or Reactotherm supplied by Krauss-Maffei or Ko-Kneter supplied by Buss), two-trough kneaders (trough mixers) and internal mixers or rotor/stator systems (eg. Dispax supplied by IKA).

In the case of sensitive active ingredients, it is preferable first for the polymeric binder to be melted in an extruder and then for the active ingredient to be admixed in a mixing/kneading reactor. On the other hand, in the case of less sensitive active ingredients, a rotor/stator system can be employed for vigorous dispersion of the active ingredient.

The mixing apparatus is charged continuously or batchwise in a conventional way depending on its design. Powdered components can be introduced in free flow, eg. through a differential weigh feeder. Plastic compositions can be fed in directly from an extruder or by a gear pump which is particularly advantageous with high viscosities and high pressures. Liquid media can be metered in through a suitable pump unit.

The mixture obtained by mixing and melting the binder and active ingredient, with or without the additive(s), is pasty or viscous (thermoplastic) and therefore also extrudable. The glass transition temperature of the mixture is below the decomposition temperature of all the components present in the mixture. The binder should preferably be soluble or swellable in a physiological medium. Examples of suitable binders are:

Polyvinylpyrrolidone (PVP), copolymers of N-vinylpyrrolidone (NVP) and vinyl esters, especially vinyl acetate, copolymers of vinyl acetate and crotonic acid, partially hydrolyzed polyvinyl acetate, polyvinyl alcohol, poly(hydroxyalkyl acrylates), poly(hydroxyalkyl methacrylates), polyacrylates and polymethacrylates (Eudragit types), copolymers of methyl methacrylate and acrylic acid, cellulose esters, cellulose ethers, in particular methylcellulose and ethylcellulose, hydroxyalkylcelluloses, in particular hydroxypropylcellulose, hydroxyalkylalkylcelluloses, in particular hydroxypropylethylcellulose, cellulose phthalates, especially cellulose acetate phthalate and hydroxypropylmethylcellulose phthalate, and mannans, especially galactomannans. The K values (method of H. Fikentscher, Cellulose-Chemie 13 (1932), 58–64 and 71–74) of the polymers are in the range from 10 to 100, preferably 12 to 70, in particular 12 to 35, and for PVP >17, in particular 20 to 35.

Preferred polymeric binders are polyvinylpyrrolidone, copolymers of N-vinylpyrrolidone and vinyl esters, poly (hydroxyalkyl acrylates), poly(hydroxyalkyl methacrylates), polyacrylates, polymethacrylates, alkylcelluloses and hydroxyalkylcelluloses.

The polymeric binder must soften or melt in the complete mixture of all the components in the range from 50 to 180° C., preferably 60 to 130° C. The glass transition temperature of the mixture must therefore be below 180° C., preferably below 130° C. If required, it is reduced by conventional pharmacologically acceptable plasticizing ancillary substances. The amount of plasticizer does not exceed 30% of the total weight of binder and plasticizer in order to form drug forms which are stable on storage and show no cold flow. However, the mixture preferably contains no plasticizer.

Examples of plasticizers of this type are:

long-chain alcohols, ethylene glycol, propylene glycol, glycerol, trimethylolpropane, triethylene glycol, butanediols, pentanols such as pentaerythritol, hexanols, polyethylene glycols, polypropylene glycols, polyethylene/propylene glycols, silicones, aromatic carboxylic esters (eg. dialkyl phthalates, trimellitic esters, benzoic esters, terephthalic esters) or aliphatic dicarboxylic esters (eg. dialkyl adipates, sebacic esters, azelaic esters, citric and tartaric esters), fatty acid esters such as glycerol mono-, di- or triacetate or sodium diethyl sulfosuccinate. The plasticizer concentration is generally from 0.5 to 15, preferably 0.5 to 5, % of the total weight of the mixture;

Examples of conventional pharmaceutical ancillary substances, whose total amount can be up to 100% of the weight of the polymer, are extenders and bulking agents such as silicates or diatomaceous earth, magnesium oxide, aluminum oxide, titanium oxide, stearic acid or its salts, eg. the magnesium or calcium salt, methylcellulose, sodium carboxymethylcellulose, talc, sucrose, lactose, cereal or corn starch, potato flour, polyvinyl alcohol, in particular in a concentration of from 0.02 to 50, preferably 0.20 to 20, % of the total weight of the mixture;

Lubricants such as aluminum and calcium stearate, talc and silicones, in a concentration of from 0.1 to 5, preferably 0.1 to 3, % of the total weight of the mixture;

Flow promoters such as animal or vegetable fats, in particular in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. It is also possible to use waxes such as carnauba wax. These fats and waxes may advantageously be admixed alone or together with mono- and/or diglycerides or phosphatides, in particular lecithin. The mono- and diglycerides are preferably derived from the above-mentioned fatty acid types. The total amount of fats, waxes, mono- and diglycerides and/or lecithins is from 0.1 to 30, preferably 0.1 to 5, % of the total weight of the composition for each layer;

Dyes such as azo dyes, organic or inorganic pigments or dyes of natural origin, with inorganic pigments in a concentration of from 0.001 to 10, preferably 0.5 to 3, % of the total weight of the mixture being preferred;

Stabilizers such as antioxidants, light stabilizers, hydroperoxide destroyers, radical scavengers, stabilizers against microbial attack.

It is furthermore possible to add wetting agents, preservatives, disintegrants, adsorbents, and mold release and blowing agents (cf., for example H. Sucker et al. Pharmazeutische Technologie, Thieme-Verlag, Stuttgart 1978).

Ancillary substances for the purpose of the invention also mean substances for producing a solid solution containing the pharmaceutical active ingredient. Examples of these ancillary substances are pentaerythritol and pentaerythritol tetraacetate, polymers such as polyethylene and polypropylene oxides and their block copolymers (poloxamers), phosphatides such as lecithin, homo- and copolymers of vinylpyrrolidone, surfactants such as polyoxyethylene 40 stearate and citric and succinic acid, bile acids, sterols and others as indicated, for example, in J. L. Ford, Pharm. Acta Helv. 61, (1986) 69–88.

Pharmaceutical ancillary substances are regarded as including bases and acids added to control the solubility of an active ingredient (see, for example, K. Thoma et al., Pharm. Ind. 51, (1989) 98–101).

The only precondition for the suitability of ancillary substances is adequate thermal stability.

Pharmaceutical active ingredients for the purpose of the invention mean all substances with a pharmaceutical effect and minimal side effects as long as they do not decompose under the processing conditions. The amount of active ingredient per dose unit and the concentration may vary within wide limits depending on the activity and release rate. The only condition is that they suffice to achieve the required effect. Thus, the concentration of active ingredient can be in the range from 0.1 to 95, preferably from 20 to 80, in particular 30 to 70, % by weight. It is also possible to employ combinations of active ingredients. Active ingredients for the purpose of the invention are also vitamins and minerals, and crop treatment agents and insecticides. The vitamins include vitamins of the A group, of the B group, meaning not only $B_1$, $B_2$, $B_6$ and $B_{12}$, and nicotinic acid and nicotinamide, but also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include peptide therapeutics.

The process according to the invention is suitable, for example, for processing the following active ingredients:

acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefatroxil, cefazolin, cefixime, cefotaxime, ceftazidime, ceftriaxone, cefuroxime, selegiline, chloramphenicol, chlorhexidine, chlor-pheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphen, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures and combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenoxymethylpenicillin, phenylephrine, phenylpropanolamine, phenytoin, piroxicam, polymyxin B, povidone-iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatotropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, folinic acid, zidovudine.

Preferred active ingredients are ibuprofen (as racemate, enantiomer or enriched enantiomer), ketoprofen, flurbiprofen, acetylsalicylic acid, verapamil, paracetamol, nifedipin or captopril.

In specific cases there may be formation of solid solutions. The term "solid solutions" is familiar to the skilled worker, for example from the literature cited at the outset. The active ingredient is present in solid solutions of pharmaceutical active ingredients in polymers in the form of a molecular dispersion in the polymer.

The resulting mixture is solvent-free, ie. it contains neither water nor an organic solvent.

Solid pharmaceutical forms which can be produced by the process according to the invention are, in particular, tablets, preferably oblong tablets, sugar-coated tablets, pastilles and pellets. The resulting drug forms can finally also be provided in a conventional way with film coatings which control the release of active ingredient or mask the taste. Suitable materials for such coatings are polyacrylates such as the Eudragit type, cellulose esters such as hydroxypropylmethylcellulose phthalates, and cellulose ethers such as ethylcellulose, hydroxypropylmethylcellulose or hydroxypropylcellulose.

It is thus possible by the process according to the invention to produce drug forms with particularly accurate dimensions. Surprisingly, this process is economical, allows very large numbers of items to be obtained per unit time and avoids any waste.

The following Examples explain the invention without limiting it. FIGS. 1 to 7 relate the Examples and are briefly described below.

BRIEF DESCRIPTION OF THE DRAWINGS

FIG. 1 depicts an extruder 10 which extrudes through dies 11 a plastic composition in the form of product extrudates which are received by a circulating conveyor belt 15. A cutting device is located at the exit from dies 11 and is, in the case of the extruder in FIG. 1, a knife 12 which breaks down the product extrudates into cylindrical shaped articles 13. The length of the shaped articles is determined by the sensor 14 which is located over each extrudate path and whose distance from the knife 12 corresponds to the length of the cylindrical shaped article 13.

Figure 1:
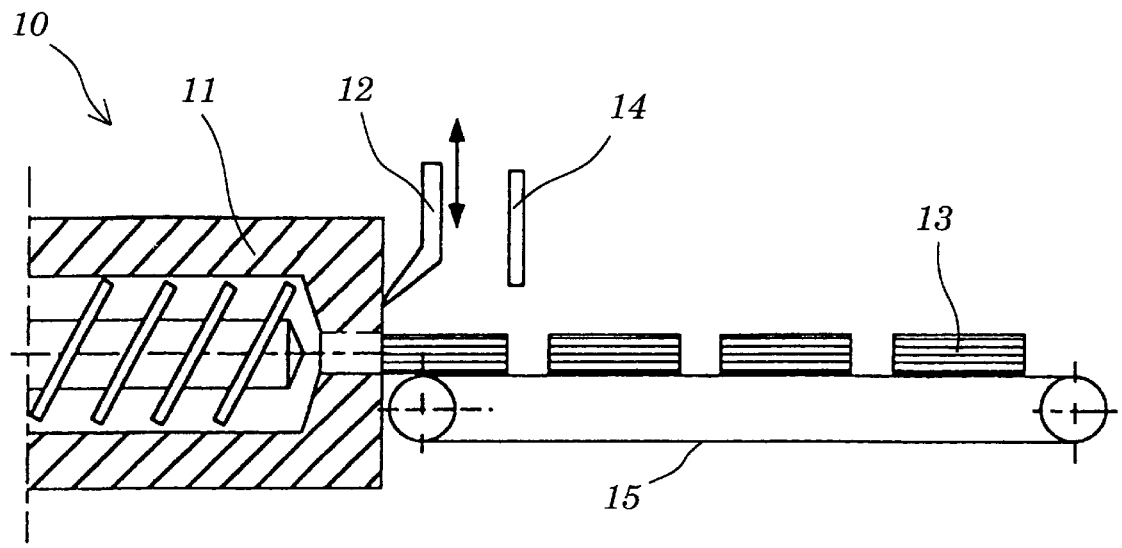
FIG. 1 shows an extruder device for the first step of the process according to the invention in longitudinal section.
Figure 2:
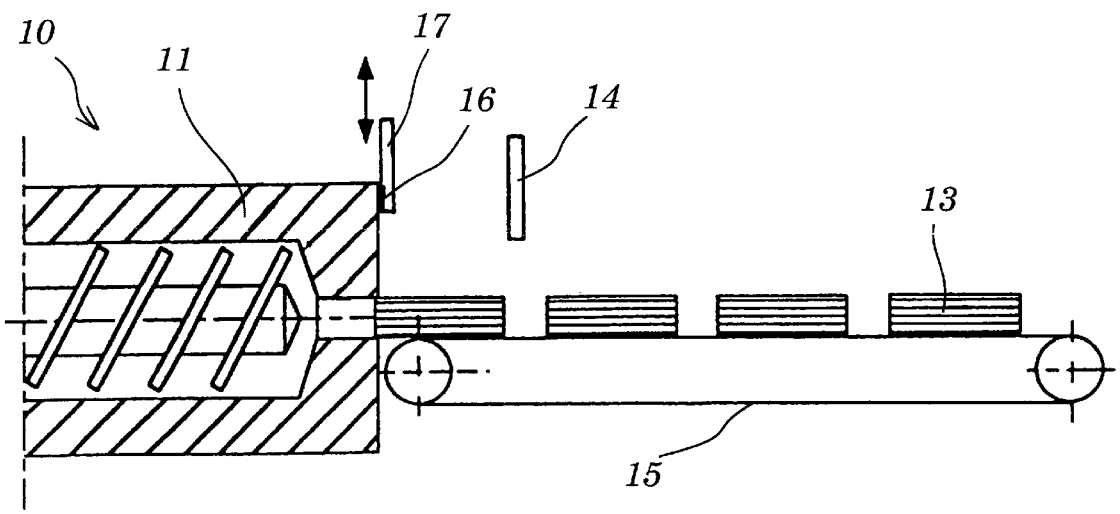
FIG. 2 shows a variant of the extruder in FIG. 1.

The embodiment of the extruder depicted in FIG. 2 differs from the embodiment in FIG. 1 essentially by a heatable wire 16 being provided as cutting device in place of the knife 12 and being located in a wire holder 17 and being movable up and down.

The knife 12 in the apparatus in FIG. 1 and the cutting wire 16 in the apparatus in FIG. 2 are controlled via the sensor 14. The sensor 14 depicts the front end of a product extrudate and then passes a control pulse to the cutting device, which sets the knife 12 or wire 16 in motion in order to produce the rear cut surface of the cylindrical shaped article 13.

Figure 3:
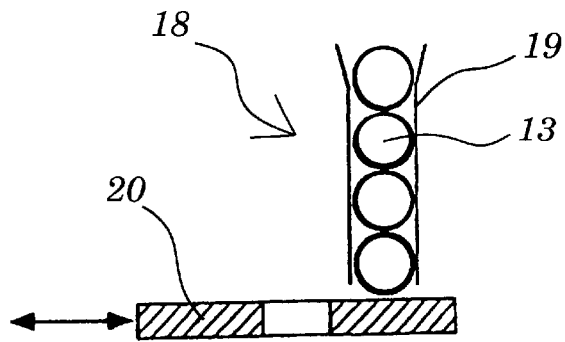
FIG. 3 shows a collector for the extruded shaped articles.

FIG. 3 depicts a collector 18 into which the extruded shaped articles 13 which have been cut to length are introduced. The collector 18 can be designed as collecting container with an upper funnel-shaped feed opening and a lower output opening. In a particularly simple embodiment of the collector 18, it can, however, also consist of two guide plates 19 which are arranged essentially parallel and whose distance apart is somewhat larger than the diameter of the cylindrical shaped article 13. In the example depicted, the guide plates 19 form a feed opening which expands in a funnel shape in the upper region. The cylindrical shaped articles 13 are arranged in the collector in FIG. 3 in a single row one on top of the other with their long axes parallel to the guide plates 19. The lower output opening of the collector 18 in the closed state is closed by a perforated slide gate 20. If a single shaped article 13 is to be discharged, the perforated slide gate 20 is moved briefly so that an elongate orifice which is present therein and whose dimensions essentially correspond to the length and width of the shaped article 13 is displaced under the opening of the collector 18 so that a single shaped article is able to fall downwards through the elongate orifice.

The discharged shaped article 13 is fed to a rounding-off tool 21.

Figure 4:
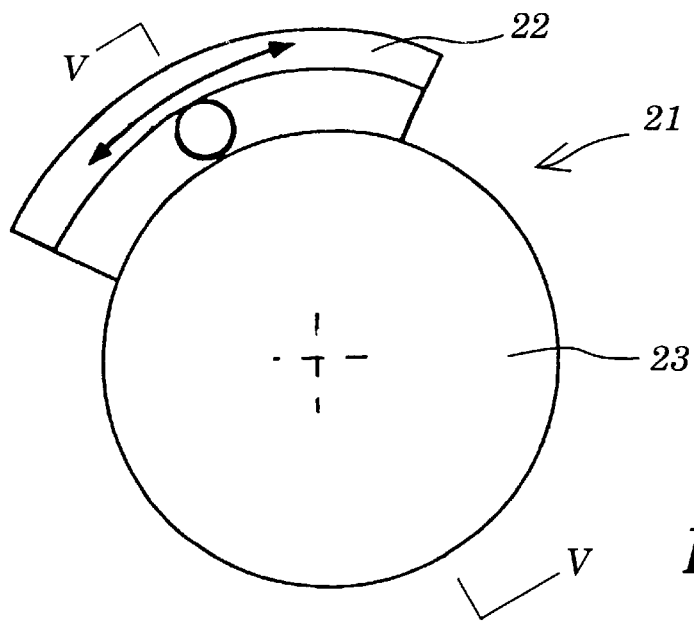
FIG. 4 shows a first embodiment of a rounding-off tool for the second step of the process according to the invention in cross section.
Figure 5:
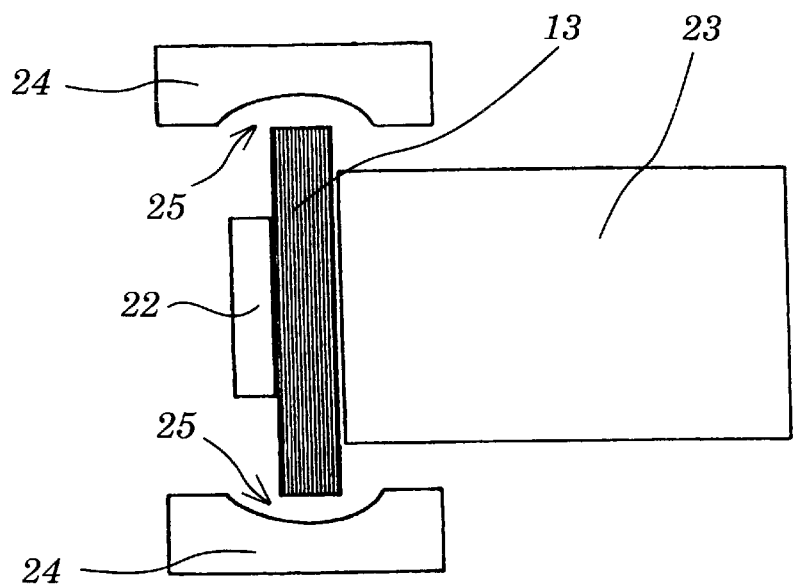
FIG. 5 shows a longitudinal section of the rounding-off tool in FIG. 4 along line V—V.

FIGS. 4 and 5 depict a first embodiment of the rounding-off tool 21. In this embodiment, the rounding-off tool consists of an arc-shaped, movable driver 22 and a stationary roll 23. The distance between the inner surface of the arc-shaped driver 22 and the outer surface of the roll 23 precisely corresponds to the diameter of the cylindrical shaped article 13. The shaped article 13 to be rounded off is arranged between the driver 22 and the stationary roll 23 so that its long axis is essentially parallel to the axis of rotation of the arc-shaped driver which can be rotated by at least the angle of a sector around the center of the stationary roll 23. The inner surface of the driver 22 comes into frictional engagement with the outer surface of the cylindrical shaped article 13 so that the shaped article 13 rolls on the stationary roll 23 when the driver 22 moves.

FIG. 5 depicts the rounding-off tool 21 in a longitudinal section along the line V—V in FIG. 4. It is evident that square jaws 24 are located in the vicinity of the two ends of the cylindrical shaped article and have a concave recess 25 on the surface facing the shaped article 13. The jaws 24 preferably consist of metal and may be heatable. They are able to move along the long axis of the cylindrical shaped article, and the centers of the concave recesses are located on this long axis. For the rounding off, the square metal jaws are continuously moved towards the smooth cut surfaces on the two ends of the cylindrical shaped article 13, while the latter is rolled backwards and forwards on the stationary roll 23 by the arc-shaped driver 22. As soon as the metal jaws are in contact with the outer edge of the end surfaces of the shaped article 13, these cut surfaces are gradually rounded off. The two mutually opposing jaws 24 approach each other until the two end surfaces of the shaped article 13 are completely rounded off.

Figure 6:
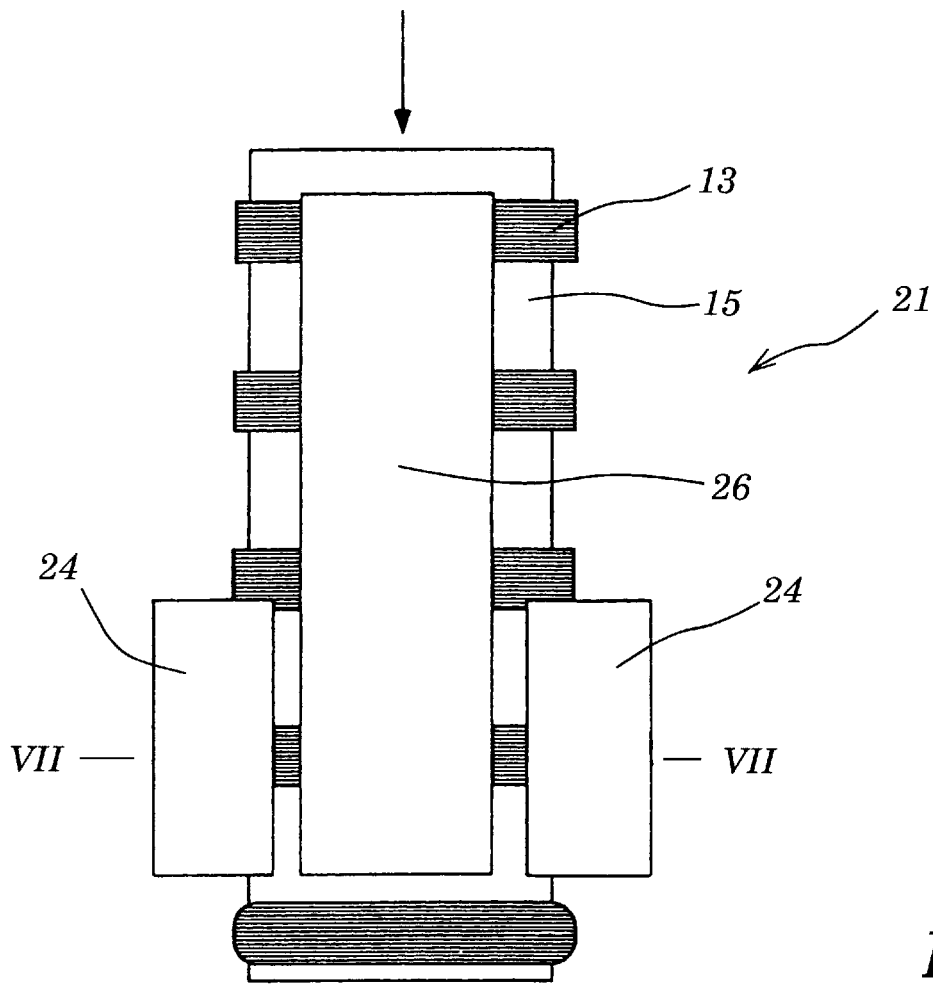
FIG. 6 shows a view of a second embodiment of the rounding-off tool for the second step of the process according to the invention.
Figure 7:
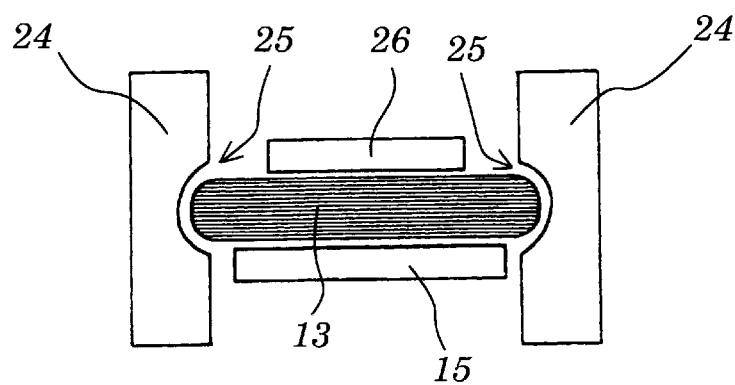
FIG. 7 shows the rounding-off tool in FIG. 6 in cross section along line VII—VII.

FIGS. 6 and 7 depict a second embodiment of the rounding-off tool 21. The cylindrical shaped articles 13 are, as in the example of FIGS. 4 and 5, moved past with their cut edges on heated square jaws 24. The recesses in the two opposing jaws 24 are essentially designed in the shape of half cylinders and taper conically in the direction of movement of the shaped articles 13. In order to set the extruded shaped articles 13 in rolling motion in the embodiment in FIGS. 6 and 7 they are rotated by 90° on the conveyor belt 15 which transports them into the rounding-off tool 21 so that their long axis is perpendicular to the direction of transport. Alternatively, it is also possible to employ a second (not depicted) conveyor belt which receives the shaped articles in the required orientation from the first conveyor belt. A plate 26 at rest is located above the conveyor belt and comes into frictional contact with the shaped articles 13 which are transported through below it and starts them rotating. The shaped articles roll virtually on the plate 26 at rest and thus reach the area of engagement of the square, conically tapering rounding-off jaws.

The method according to the invention is illustrated by two examples hereinafter.

EXAMPLE 1

Production of Oblong Tablets using a Twin Screw Extruder

A polymer/active ingredient mixture (300 kg of polyvinylpyrrolidone with K value 30, 6 kg of Aerosil 90, 54 kg of maltodextrin, 240 kg of ibuprofen) is prepared with a meshing, self-cleaning corotating twin screw extruder 10 with a screw diameter of 57 mm. The plastic composition is extruded at an output of 100 kg/h through ten dies 11 which are arranged in a line and each have a diameter of 8 mm, and is received by a circulating conveyor belt 15. The belt moves at the speed of the emerging extrudate. In the present case, the speed is about 0.85 m/min at an extrudate density of ~1 g/cm³. A sensor 14 is arranged over each extrudate path, and its distance from the die corresponds to the length of an oblong tablet. When the sensor locates the start of an extrudate it sends a pulse to the cutting device and sets this in motion in order to execute the cut. It is possible to use as cutting tool a knife 12 (FIG. 1), which returns to the starting position immediately after the cut, or a wire 16 (FIG. 2) which may be heatable and which can execute a cut both in the downward and in the upward movement. The cutting rate for an oblong tablet length of about 2 cm is –50/min.

The cylindrical shaped articles 13 which have cooled on the belt are temporarily stored in a collector 18 (FIG. 3) and subsequently fed through a perforated slide gate 20 singly into a rounding-off tool 21 (FIG. 4). During this, an arc-shaped driver 22 holds and moves a shaped article 13, and thus sets it in rotation around its long axis, in contact with a stationary roll 23. While the shaped article executes the rotational movement, its flat ends are passed by a heated rounding-off tool (FIG. 5). The rounding-off tool consists of metal jaws 24 which are arranged in pairs and have, on the sides facing the shaped article 13, concave recesses 25. The two metal jaws can be moved along the long axis of the shaped articles 13, and the centers of the recesses in the shape of segments of a sphere are located on this long axis. The shaped article 13 is rounded off as described previously, with the edge circumference of the shaped article continuously decreasing with progressive movement of the metal jaws. The movement of the metal jaws 24 stops when the circumference of the edges reaches zero and, as a consequence, the entire cross-sectional areas of the rounded-off shaped articles 13 are in contact with at least part of the recess in the shape of a segment of a sphere.

An oblong tablet is obtained without producing any waste. At the end of the rounding-off step, the tablet is discharged from the process.

The oblong tablets obtained in this way can be subjected to a subsequent treatment, for example coating steps, or fed directly to packaging.

EXAMPLE 2

Production of Oblong Tablets using a ko-nekter

A ko-nekter with a diameter of 70 mm is used in place of the twin screw extruder used in Example 1. This ko-nekter brings about a particularly vigorous mixing step because a backward and forward movement is superimposed on the rotational movement. The prepared plastic composition is discharged at an output of 100 kg/h by a gear pump which ensures uniform discharge and through dies. The circular extrudate is cut as described in Example 1. The cylindrical sections 7 are rotated by 90° on the conveyor belt 15 so that they execute a translational movement perpendicular to their long axis between the belt and the stationary belt 26, this movement being in the same direction as the movement of the conveyor belt (FIG. 6). During this, the shaped articles 13 also rotate around their long axis. The flat surfaces are rounded off in a similar manner to Example 1 on rounding-off jaws 24 which have semi-cylindrical, conically tapering recesses 25 (FIG. 7).

Once again, after completion of the rounding-off step, the oblong tablet can be subjected to a subsequent coating step or packed directly.

We claim:

1. A process for producing solid drug forms by mixing and melting at least one pharmacologically acceptable polymeric binder and at least one pharmaceutical active ingredient, with or without conventional pharmaceutical additives, in the absence of a solvent to give a plastic mixture and extruding the plastic mixture to give an extrudate and shaping the extrudate, wherein the solid drug form is an oblong tablet, and wherein the shaping of the extrudate comprises two separate, consecutive steps a) first breaking the extrudate into shaped articles, and folding said shaped articles towards a rounding-off tool b) subsequently rounding off the edges and corners of the shaped articles in the plastic state to give the oblong tablet.

2. A process as claimed in claim 1, wherein the plastic mixture is extruded as extrudate with circular cross-section.

3. A process as claimed in claim 2, wherein the shaped articles are cylinders with a length/diameter ratio of more than 1.

4. A process as claimed in claim 1, wherein the breaking down of the plastic mixture takes place by cutting.

5. A process as claimed in claim 1, wherein rounding off takes place by contact between the shaped article and at least one rounding-off tool which may be heated.

6. A process as claimed in claim 5, wherein the shaped article and/or the rounding-off tool is moved.

* * * * *

UNITED STATES PATENT AND TRADEMARK OFFICE
CERTIFICATE OF CORRECTION

PATENT NO.: 6,051,253

DATED: April 18, 2000

INVENTOR(S): ZETTLER et al.

It is certified that error appears in the above-identified patent and that said Letters Patent is hereby corrected as shown below:

Col. 10, claim 1, line 34, "folding" should be --feeding--.

Signed and Sealed this

Twenty-seventh Day of March, 2001

Attest:

NICHOLAS P. GODICI

Attesting Officer

Acting Director of the United States Patent and Trademark Office